United States Patent [19]

Nestor

[11] Patent Number: 4,800,886
[45] Date of Patent: Jan. 31, 1989

[54] SENSOR FOR MEASURING THE CONCENTRATION OF A GASEOUS COMPONENT IN A FLUID BY ABSORPTION

[75] Inventor: James R. Nestor, Nashua, N.H.
[73] Assignee: C. R. Bard, Inc., Murray Hill, N.J.
[21] Appl. No.: 885,072
[22] Filed: Jul. 14, 1986
[51] Int. Cl.$^4$ ................................................ A61B 5/00
[52] U.S. Cl. ...................................... 128/634; 128/664;
128/666; 356/437; 356/440
[58] Field of Search ............... 128/633, 634, 664, 665,
128/666; 356/436, 437, 440

[56] References Cited

U.S. PATENT DOCUMENTS

| Re. 31,879 | 5/1985 | Lübbers et al. | 436/133 |
|---|---|---|---|
| 3,068,739 | 12/1962 | Hicks et al. | 128/634 |
| 3,123,066 | 3/1964 | Brumley | 128/634 |
| 3,856,404 | 12/1974 | Hershler | 356/437 |
| 4,050,450 | 9/1977 | Polanyi et al. | 128/2 |
| 4,201,222 | 5/1980 | Haase | 128/634 |
| 4,321,057 | 3/1982 | Buckles | 23/230 |
| 4,399,099 | 8/1983 | Buckles | 422/58 |
| 4,476,870 | 10/1984 | Peterson et al. | 128/634 |
| 4,509,522 | 4/1985 | Manuccia et al. | 128/634 |
| 4,560,248 | 12/1985 | Cramp et al. | 128/634 |
| 4,622,974 | 11/1986 | Coleman | 128/634 |
| 4,682,895 | 7/1987 | Costello | 128/634 |

FOREIGN PATENT DOCUMENTS

| 0073558 | 3/1983 | European Pat. Off. | 128/634 |
|---|---|---|---|
| WO81/00912 | 4/1981 | PCT Int'l Appl. | |
| 2160646A | 12/1985 | United Kingdom. | |

OTHER PUBLICATIONS

Coleman et al., "Fiber Optic Based Sensor for Bioanalytical Absorbance Measurements", 56 Anal. Chem., 2246-2249 (1984).
G. Vurek et al., "A Fiber Optic PCO$_2$ Sensor", 11 Annals of Biomedical Engineering, 499–510 (1983).
W. R. Seitz, "Chemical Sensors Based on Fiber Optics", Analytical Chemistry, vol. 56, No. 1, Jan. 1984, pp. 16A-43A.

Primary Examiner—Edward M. Coven
Assistant Examiner—John C. Hanley
Attorney, Agent, or Firm—Wolf, Greenfield & Sacks

[57] ABSTRACT

Apparatus and methods are provided for determining the concentration of a gaseous component in a fluid. A solid body of a natural or synthetic high polymer, which is permeable to the gaseous component, is exposed to the fluid, the polymer is exposed to infrared radiation, and the infrared absorption by the gas in the polymer is measured. In the preferred embodiment, a sensor is provided for making in vivo measurements of the concentration of $CO_2$ in the blood. The sensor includes an optical fiber which is nonpermeable to $CO_2$ and substantially transparent at the $CO_2$ absorption wavelength range, and a solid body of polymeric material at the distal end of the fiber which is substantially transparent to the absorption wavelength range and permeable to $CO_2$. An incident infrared signal is transmitted down the fiber, passes through the body, is reflected off the distal end of the body, and the intensity of the return signal is measured by a detector. The return signal is diminished in proportion to the concentration of the $CO_2$ in the polymeric body. The sensor is disposed within a catheter and is positionable within the narrow blood vessels of the body for continuous real time monitoring of the carbon dioxide concentration of the blood.

28 Claims, 3 Drawing Sheets

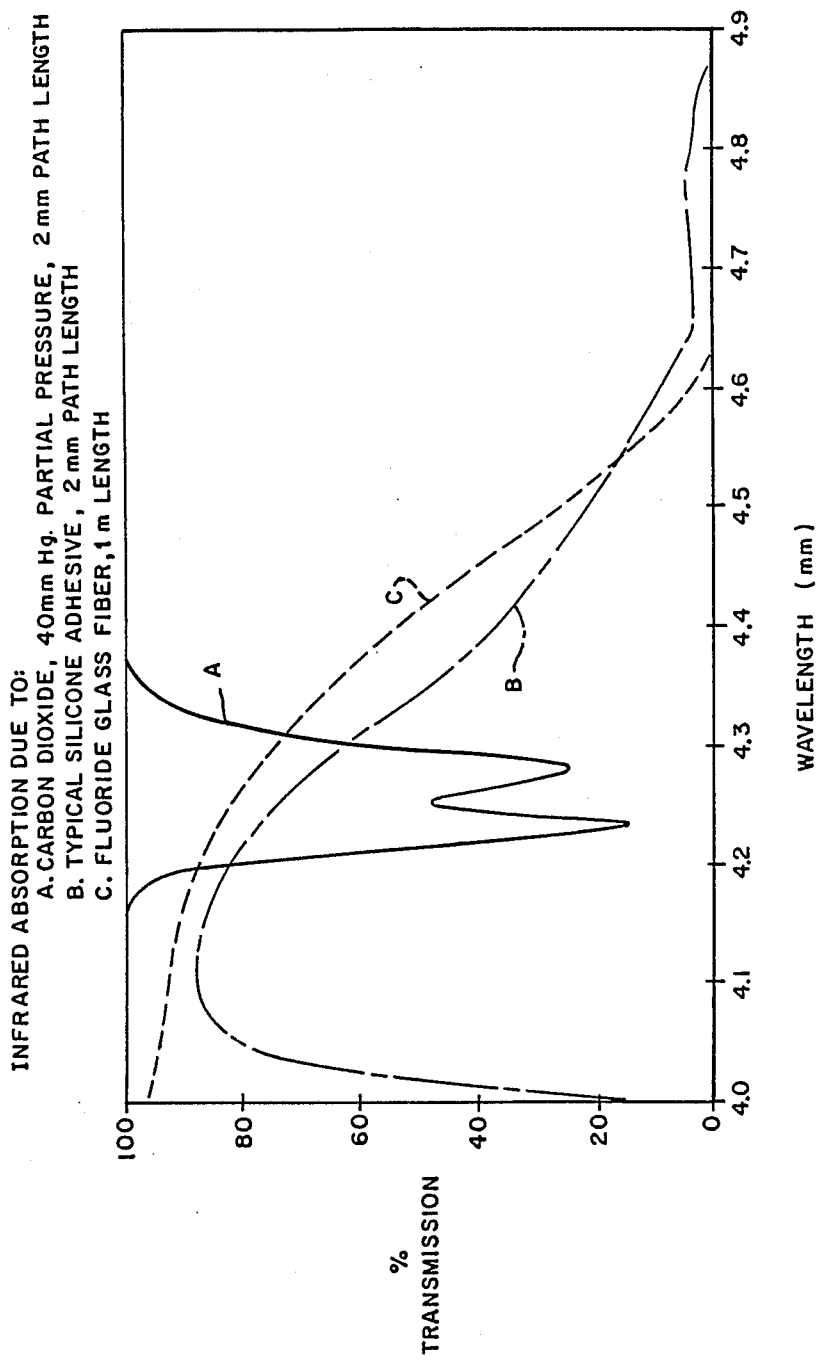

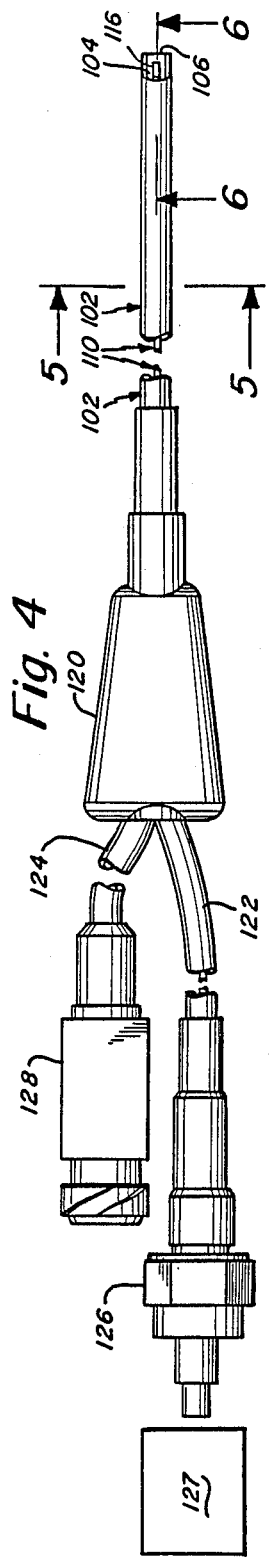
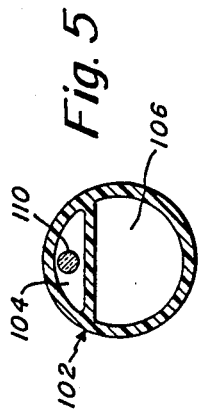
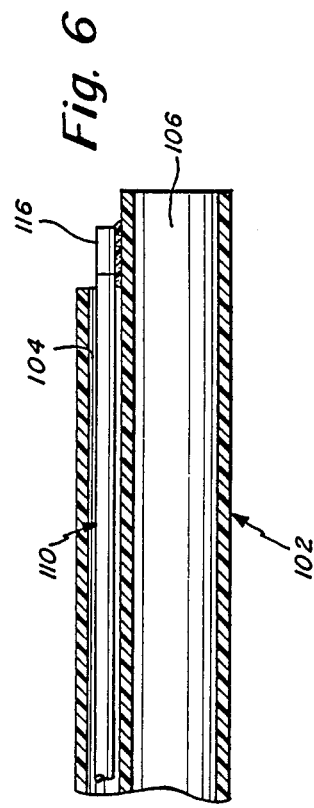

SENSOR FOR MEASURING THE CONCENTRATION OF A GASEOUS COMPONENT IN A FLUID BY ABSORPTION

BACKGROUND OF THE INVENTION

This invention relates to a sensor for determining the concentration of a gaseous component in a fluid by absorption and, in the preferred embodiment, to a fiber optic probe for making in vivo measurements of the partial pressure of carbon dioxide in the blood.

Blood gas analysis is performed on nearly every hospital patient both during and after surgery. The analysis is concerned primarily with three parameters—the partial pressures of oxygen and carbon dioxide, the $PO_2$ and $PCO_2$, and the negative logarithm of hydrogen ion activity, the pH. These three parameters give a good indication of the patient's cardiac, respiratory and circulatory functioning and of metabolism. Monitoring the level of carbon dioxide in the blood alone gives a good indication of proper functioning in all of these systems because carbon dioxide, a waste product of metabolism, travels through the circulatory system and is removed through the respiratory system.

Several sophisticated blood gas analyzers are commercially available for analyzing blood samples after the blood is extracted from the patient (in vitro). The withdrawal and subsequent analysis of a blood sample is both cumbersome and time-consuming and does not allow for continuous monitoring of the concentrations of gases dissolved in a patient's blood. There has been a need for many years for a system which would enable blood gas measurements to be made directly in the patient (in vivo), thereby avoiding the difficulties and expense inherent in the in vitro techniques.

Among the suggestions in the prior art was the use of indwelling electrode probes for continuous monitoring of the blood gas. The in vivo electrode probes have not been acceptable. Two principal disadvantages of the electrode probes are the danger of using electrical currents in the body and the difficulty in properly calibrating the electrodes.

Also among the suggested techniques for in vivo measurement have been the use of fiber optic systems. In a fiber optic system, light from a suitable source travels along an optically conducting fiber to its distal end where it undergoes some change caused by interaction between the light and a component of the medium in which the probe is inserted or interaction with a material contained in the probe tip which is sensitive to (i.e., modified by) a component in the medium. The modified light returns along the same or another fiber to a light-measuring instrument which interprets the return light signal.

Fiber optic sensors appear to offer several potential benefits. A fiber optic sensor is safe, involving no electrical currents in the body. The optical fibers are very small and flexible, allowing placement in the very small blood vessels of the heart. The materials used, i.e., plastic, metal, and glass, are suitable for long-term implantation. With fiber optic sensing, existing optical measurement techniques could be adapted to provide a highly localized measurement. Light intensity measurements could be processed for direct readout by standard analogue and digital circuitry or a microprocessor. However, although the potential benefits of an indwelling fiber optic sensor have long been recognized, they have not yet been realized in a viable commercial product.

Among the principal difficulties has been in the development of a sensor in a sufficiently small size which is capable of relatively simple and economical manufacture so that it may be disposable.

One type of in vivo fiber optic blood gas sensor proposed in the prior art involves the transmission of light directly into the blood. Light travels down the fiber and is allowed to leave the fiber at the distal end to interact directly with the blood and to report back via the return signal some characteristic spectroscopic property of the blood. An absorption sensor of this type is described in U.S. Pat. No. 4,509,522 to Manuccia et al., wherein absorption occurs as an incident light beam travels through the blood flowing between the ends of two chopped fibers, or as the beam travels through the blood flowing between the distal end of a fiber and a spaced mirror. These devices are complex and difficult to manufacture.

A similar fiber optic sensor for measuring the concentration of bilirubin in the blood is described in Coleman et al., "Fiber Optic Based Sensor For Bioanalytical Absorbance Measurements," 56 Anal. Chem. 2246–2249 (1984). The authors state that a sample chamber having a well-defined optical path length is necessary to obtain true absorbance values, and they propose a sensor having a single optical fiber in order to achieve a very small size. The Coleman et al. sensor consists of an optical fiber disposed in a needle and spaced from the distal end thereof, an aluminum foil reflector disposed at the end of the needle, and apertures in the needle to allow blood to flow into the chamber defined within the needle between the distal end of the fiber and the reflector. The needle and fiber assembly is then inserted into a larger gauge needle. Again, this device is difficult to construct and use of the rigid needle prohibits advancing the same through the blood vessels.

In another type of proposed blood gas sensor, the gas component to be measured is separated from the blood while making the spectroscopic determination. A gas-permeable membrane is used to form a chamber at the distal end of the fiber. The spectroscopic determination is made within the chamber either directly with the diffused component or with an intermediate reagent contained in the chamber. For example, U.S. Pat. No. 4,201,222 to Haase describes an optical catheter having at its distal end an absorption chamber in which a direct absorption measurement is made, formed by a cylindrical housing and a distensible semipermeable diaphram. The diaphram is silicon [sic] rubber which permits diffusion of oxygen and carbon dioxide into the chamber. A reflective coating of vacuum deposited or evaporated gold or aluminum is applied to the interior surface of the diaphram to prevent light from escaping. Two sources of light, one visible red for absorption by oxygen and the other infrared for absorption by carbon dioxide, are alternately pulsed down the fiber. The resiliently deformable diaphram also allows monitoring of blood pressure and pulse rate. Again however, the rigid sample chamber is difficult to construct in small size.

A fiber optic $PCO_2$ sensor having an intermediate reagent is described in G. Vurek, et al., "A Fiber Optic $PCO_2$ Sensor," 11 Annals of Biomedical Engineering 499–510 (1983). The sensor is made with plastic fibers and has at its distal end a silicone rubber tube filled with a phenol red-$KHCO_3$ solution. The ambient $PCO_2$ controls the pH of the bicarbonate buffer solution which influences the optical transmittance of the phenol red.

The resulting electrical signal is said to be linearly related to the PCO$_2$ over a certain range. However, a problem with shifts in the calibration curve is noted due to deformation of the flexible silicone tube.

A PO$_2$ sensor probe utilizing a fluorescent intermediate reagent is described in U.S. Pat. No. 4,476,870 to Peterson et al. The probe, which operates under the principle of oxygen quenching of dye fluorescence, includes two plastic fibers ending in a section of porous polymer tubing serving as a jacket for the fibers. The tubing is packed with a fluorescent light-excitable dye placed on a adsorptive polymeric beads. The polymeric adsorbent is said to avoid the problem of humidity sensitivity found with inorganic adsorbents such as silica gel. Again, it is difficult to construct this jacket and bead configuration in a small size.

Still another approach is suggested in U.S. Pat. Nos. 4,399,099 and 4,321,057, to Buckles. In Buckles apparatus for biochemical analysis, the optical fiber itself serves as the medium in which the spectroscopic change occurs. The fiber, which is permeable to the blood gas of interest, absorbs the gas. The absorbed gas affects the light that emerges from the exit end of the fiber in proportion to the concentration of the gas in the sample fluid in contact with the fiber. However, because the fiber is permeable to the gas there is no way to control the path length over which absorbance occurs. Even if a nonpermeable coating covers all but a fixed portion of the fiber, there is no way to prevent the analyte from permeating along the length of the fiber thereby creating an indeterminate length of measurement. Without knowledge of the path length, an accurate absorbance measurement cannot be made. In other embodiments, the spectroscopic change occurs in one or more sheaths surrounding the optical fiber which may contain an intermediate reagent.

Thus, in spite of the great need for an in vivo fiber optic sensor, none of the proposed sensors has met with commercial success. Generally, they are either not reliable or not adapted for production manufacturing techniques. Devices involving sample chambers are difficult if not impossible to make in a miniature size required for use in the blood vessels. Other sensor probes are not flexible enough to be threaded through the narrow blood vessels.

It is an object of this invention to provide an in vivo sensor for the continuous real time monitoring of the concentration of a gaseous component in a body fluid, such as the carbon dioxide concentration of the blood.

It is another object of this invention to provide a very small and flexible fiber optic catheter that can be easily advanced through the small blood vessels and cavities of the body.

Still another object is to provide a fiber optic sensor which is both reliable and adapted for production manufacturing techniques.

A still further object is to provide a sensor having a fixed path length for absorption in order to obtain reliable absorbance measurements.

SUMMARY OF THE INVENTION

According to the invention, apparatus is provided for measuring the concentration of a gaseous component in a fluid by absorption, where the gaseous component has an energy absorption peak in a predetermined wavelength range. The apparatus includes a waveguide means, such as an optical fiber or a hollow or liquid-filled waveguide. The waveguide means has an inlet aperture for receiving an incident energy signal within the predetermined wavelength range and an emission aperture for emitting an emitted energy signal. The waveguide means is substantially transparent to energy within the predetermined wavelength range. A segment of the waveguide means consists of a fixed length body of solid material which is permeable to the gaseous component. The remainder of the waveguide means is substantially impermeable to the gaseous component. The waveguide means is constructed and arranged so that the segment is exposed to the fluid to enable the gaseous component to permeate the segment and absorb the incident energy signal along the fixed length of the body to thereby reduce the intensity of the emitted energy signal in proportion to the concentration of the gaseous component in the fluid. The difference in intensities of the incident and emitted energy signals is used to determine the concentration of the gaseous component in the fluid.

In a preferred embodiment, the sensor apparatus is disposed in a flexible catheter and is insertable into the body cavities, such as the blood vessels, for continuous in vivo monitoring of the concentration of a gaseous component in a body fluid. Preferably the waveguide means is a single optical fiber which allows the catheter to be made in a very small diameter. Preferably, the segment consists of a coaxial cylinder of a solid polymeric material which is directly adhered to the distal end of the fiber. A reflective coating covers the distal end of the segment for reflecting the energy signal back through the segment and down the optical fiber to a detector. More preferably, all outer surfaces of the segment, except for the surface attached to the fiber, are at least partially coated with a reflective metal coating for maintaining the light-guiding properties of the segment yet permitting gas to permeate through the coating into the segment.

In order to obtain an accurate absorbance measurement, it is essential that the segment have a fixed length so that the path length over which energy is absorbed by the gaseous component is known and fixed. Because the fiber is nonpermeable to the gaseous component, it does not contribute to the path length along which absorption occurs. The path length is selected based upon the concentration to be measured and the absorption coefficient of the gaseous component in order to attain a readily detectable change in intensity for a change in concentration.

In the preferred embodiment, the sensor is adapted for measuring the concentration of carbon dioxide. Carbon dioxide has a spectrally isolated absorption peak in the infrared region with respect to other physiological gases (e.g., oxygen and water vapor). Thus, this sensor is particularly useful in a physiological environment such as for in vivo measurement of the carbon dioxide concentration of the blood. The predetermined absorption wavelength range for carbon dioxide is between about 4.1 and 4.4 micrometers, and more specifically of from about 4.16 to about 4.36 micrometers. Infrared transmitting fibers are available which are substantially transparant at this wavelength range and which are nonpermeable to carbon dioxide. Suitable polymeric materials are also available to define the gas permeable segment which are both permeable to carbon dioxide and substantially transparent to the absorption wavelength range.

In an especially preferred embodiment of the in vivo CO$_2$ sensor, a single infrared transmitting fiber, such as a heavy metal fluoride glass, is used. A solid cylindrical body of polymeric material is directly bonded to and coaxial with the distal end of the fiber. A preferred polymer is silicone, which has a high value of carbon dioxide permeability and is substantially transparent at the absorption wavelength range. A reflective metal coating is provided at the distal end of the body, and more preferably on a substantial portion of the outer surface of the body in order to preserve the light-guiding properties of the body. The composite fiber and sensor is insertable within a flexible catheter for positioning the sensor within a body cavity, such as narrow blood vessels.

The invention further includes a method for determining the concentration of a gaseous component in a fluid by absorption. The method consists of contacting a polymeric body with the fluid containing the gaseous component, exposing the body to infrared radiation, and measuring the infrared absorption in the body by the gaseous component. The body may be any of various natural or synthetic high polymers which have a substantial affinity for the gaseous component and which are substantially transparent to infrared radiation at the absorption wavelength of the gaseous component. The method is useful for determining the concentration of gases such as carbon dioxide, water vapor, nitrous oxide, halogenated hydrocarbons, ethyl alcohol, or anesthetic gases.

BRIEF DESCRIPTION OF THE DRAWINGS

FIG. 3 is a graphical illustration of the energy absorption curves for the optical fiber, the sensor body, and for carbon dioxide.

FIG. 4 is a fragmented illustration of a catheter embodying the fiber optic sensor.

FIG. 5 is a cross-sectional view taken along section lines 5—5 of FIG. 4 showing the catheter lumens.

FIG. 6 is a partial sectional view taken along section lines 6—6 of FIG. 4 showing the distal end of the catheter.

DETAILED DESCRIPTION OF THE PREFERRED EMBODIMENTS

A preferred embodiment of this invention consists of a sensor for in vivo measurement of the concentration of carbon dioxide in a body fluid, such as the blood, wherein the sensor includes a single optical fiber waveguide having attached at one end a cylindrical body of polymeric material of fixed length defining a gas-absorbing region. Both the fiber and body are substantially transparent to the energy absorption peak for carbon dioxide. The body is permeable to carbon dioxide while the fiber is substantially impermeable to carbon dioxide. The distal end of the body is provided with a reflective coating. An incident energy signal is directed into the proximal end of the fiber and is transmitted along the fiber to the distal end and then into the body. The incident signal makes a first pass along the fixed length of the body, is reflected off the reflective coating, and returns to make a second pass along the fixed length of the body and is then transmitted down the fiber back to the proximal end of the fiber and directed to a detector. The sensor thus provides a known and fixed absorption path length equal to twice the fixed length of the body. Knowing this path length, the absorption coefficient of the body for carbon dioxide, and measuring the intensity of the emitted energy signal in relation to the incident signal, the partial pressure of carbon dioxide can be calculated.

Although the preferred embodiment is directed to an in vivo fiber optic $CO_2$ sensor, the invention is not limited to in vivo sensors, nor to carbon dioxide sensors, nor to fiber optic waveguide means. Nonfiber waveguide means may be used such as, for example, a hollow or liquid-filled waveguide. The principal requirement is that the waveguide means be impermeable to the gas being measured. If fiber optics are used, a plurality of fibers in a bundle may be used. Alternatively, the gas permeable segment may be interposed between the abutting ends of two glass fibers, with one fiber leading to the incident energy source and the second fiber to the detector. Thus, the gas permeable segment may be disposed either at the distal end of the nonpermeable waveguide means or at any other point along its length, and rather than a reflective coating, a second optical fiber can be used for returning the partially absorbed signal which has passed through the segment to the detector. In addition, other gases having spectrally isolated absorption peaks can be measured with the sensor of this invention.

Figure 1:
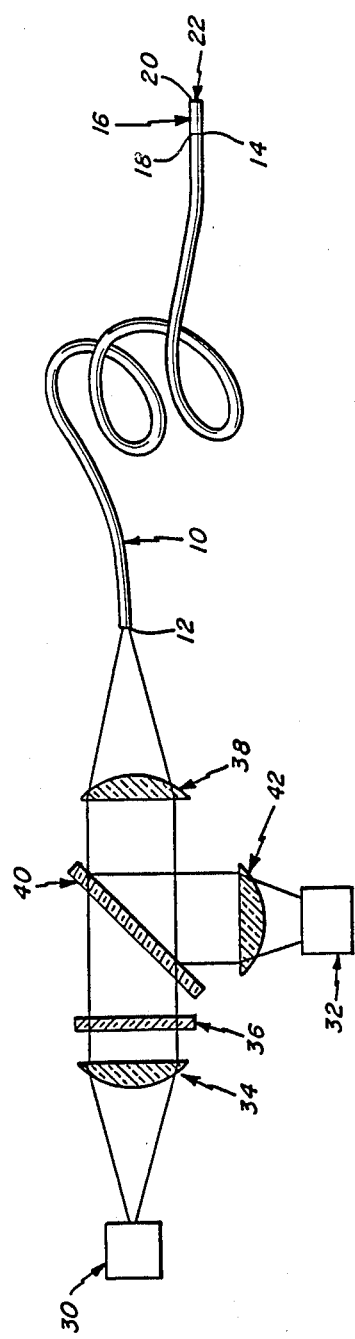
FIG. 1 is a schematic drawing of the fiber optic sensor of this invention and associated instrumentation.

The preferred fiber optic sensor of this invention and associated apparatus is shown in FIG. 1. The sensor includes an optical fiber 10 having a proximal end 12 and a distal end 14. The sensor further includes a solid body 16 of a selected length defined by first and second ends 18, 20. The first end 18 is disposed adjacent the distal end of the fiber and the second end 20 has an inwardly reflective surface 22.

The apparatus to the left of the sensor fiber in FIG. 1 consists of a radiation source 30, a detector 32, and various optical elements Preferably, an incoherent energy source 30, such as a black body radiator, produces broadband radiation which is partially collected and collimated by a lens 34. The collimated signal from the lens is received by a narrowband filter 36 which rejects nearly all the radiation from the source except for a narrow segment which includes part or all of the predetermined wavelength range for which the gaseous component to be measured is selectively absorptive. This narrowband signal is imaged onto the face at the proximal end of the fiber by a second lens 38. The face at proximal end 12 thus defines an inlet aperture for receiving the incident energy signal. The radiation travels to the distal end of the fiber where it passes directly into a gas-absorbing region defined by the body 16. The radiation then encounters a mirrored retro-reflector 22 and retraces its path back through the fiber 10 and exits the proximal end 12 of the fiber. The proximal end thus defines an emission aperture from which the emitted energy signal exits, as well as the inlet aperture. The emitted signal then passes through lens 38 to a partially reflecting mirror 40 and third lens 42 for focusing it onto the active area of a detector 32.

The return signal is diminished in intensity over the predetermined wavelength range in proportion to the concentration of the gaseous component in the gas-absorbing region The detector measures the intensity of the emitted signal. By comparing the output of the detector with a calibration curve for the system, the concentration of the gaseous component can be determined.

The calibration curve is determined by making at least two measurements with the system for known concentrations of the gaseous component, and constructing a line determined by those points. The output of the detector in the absence of the gaseous component constitutes the intensity of the incident signal minus any system losses. After this initial one-time calibration, a reference energy signal outside of the predetermined wavelength range may be sent along with the absorption signal and separately detected in order to continuously monitor the optical alignment of the system and system losses during operation.

Figure 2:
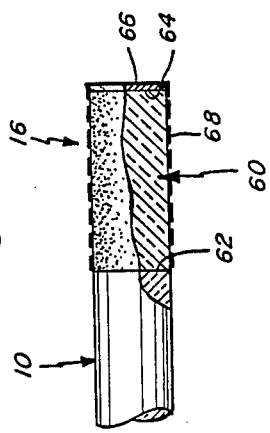
FIG. 2 is a partial sectional view of the distal end of the fiber optic sensor.

A preferred sensor body 16 is shown in FIG. 2. A gas-absorbing region 60 is composed of a solid cylindrical polymeric body which is directly bonded at its proximal end 62 to the exit face at the distal end of the optical fiber 10. The region 60 has substantially the same diameter as the fiber. The gas-permeable polymer material has a high value of solubility for the gaseous component of interest and is optically clear at the predetermined wavelength range defined by the absorption peak of the gaseous component. The region 60 is covered at its distal end 64 with a plane metal reflective coating 66, and preferably, except for proximal end 62, the entire outer surface 68 of the body is partially covered with a very thin reflective coating 68 in order to preserve the light-guiding properties of the body. Such a partial and very thin (e.g., 2–5 micron) coating of metal, e.g., aluminum, gold, silver or nickel, can be formed by electrodeposition or vacuum deposition, to be both reflective and still gas permeable.

In an alternative embodiment, not shown, the sensor body 16 is disposed between two segments of an optic fiber. In this alternative embodiment the inlet and emission apertures are not the same, rather the incident energy enters one end (inlet aperture) of a first optic fiber segment, the signal travels through the first optic fiber segment, the sensor body, and the second optic fiber segment in succession, and then exits from the opposing end (emission aperture) of the second optic fiber segment.

The fiber optic sensor of this invention can be inserted into a blood vessel or body cavity via a flexible catheter as shown in FIGS. 4–6. The catheter is formed from an elongate flexible body 102 and, for example, may be extruded from an appropriate plastic material such as polyurethane or polyvinyl chloride. The body 102 has a first lumen 104 in which the optical fiber 110 of the sensor is enclosed and a second lumen 106 for fluid infusion. Both of lumens 102 and 106 are open at their distal ends.

The proximal end of the catheter includes a molded fitting 120 which is secured to the catheter body 102. Projecting from the proximal end of the fitting 120 are a pair of flexible tubes 122, 124. The tube 122 is adapted to receive the optical fiber 110, which extends through the fitting 120. The proximal end of the tube 122 is provided with a connector 126 which is connected to the proximal end of the optical fiber 110. Connector 126 is adapted to be mounted with respect to a source of radiant energy, such as a laser or black body radiator (illustrated diagramatically at 127) so that the proximal end of the optical fiber 110 may receive the radiant energy and conduct it along its length to the distal end of the fiber.

The small lumen 104 is skived back from the distal end of the catheter body 102, leaving the large lumen (106) extending distally of the small lumen opening. The optical fiber 110 extends slightly beyond the end of the small lumen opening and is epoxied in place. This allows the optical sensor to be in contact with the blood.

The other tube 124 at the proximal end of the catheter communicates through the fitting 120 with the second lumen 106 of the catheter body 102 and preferably is provided with a conventional luer connector 128. The pathway thus defined between the luer connector 128, tube 124, and main catheter body 102 provides for communication with the distal region of the patient's blood vessel or body cavity where the distal end of the catheter is located. It provides a passageway for fluids to flow both to and from the distal region and also provides a means for making pressure measurements as well as infusion or withdrawal of various fluids.

The sensor of this invention is especially useful for determining the concentration of carbon dioxide in a fluid sample. Carbon dioxide, in the gas phase, has an intense and spectrally isolated absorption envelope centered at 2,349 $cm^{-1}$ (4.257 micrometers). The envelope lies substantially within the wavelength range of about 4.16 to about 4.36 micrometers, as shown in FIG. 3. This envelope is made up of hundreds of discrete closely-spaced narrow bands or lines. When mixed with other physiologically important gases at unreduced pressure, the discrete lines are broadened and blended to some extent due to collisions and interactions. However, the envelope remains within a sufficiently narrow band of about 0.2 micrometers so as to permit ready detection by an incident signal having a spectral width of about one half as much, or about 0.1 micrometer. The output of a broadband source, such as a black body radiator, can be filtered to produce such a spectral width.

There are laser sources which can produce an incident signal to coincide with the frequency of one of the individual carbon dioxide absorption lines, such as a tunable lead-salt diode laser However, it is difficult to maintain the frequency alignment for such a narrow band Therefore, because it is easier to hold the frequency alignment and because the source is cheaper, it is preferred in many instances to use a broadband source having 0.1 micrometer or more of spectral width to cover the entire envelope.

At its maximum, the absorption coefficient of the $CO_2$ absorption envelope is about 100 $cm^{-1}$ $atm^{-1}$. This value would produce a unity optical absorbance in a 2 mm path length of $CO_2$ at a partial pressure of 40 mm Hg. The partial pressure of carbon dioxide in the blood is typically 40 mm Hg.

Because carbon dioxide has this spectrally isolated absorption envelope having a large absorption coefficient, carbon dioxide can be successfully detected in the presence of other physiological gases via an absorption technique. As shown in FIG. 3, carbon dioxide has an absorption wavelength range centered at about 4.26 micrometers and extending from about 4.16 to about 4.36 micrometers.

A body material is selected which is permeable to carbon dioxide but which is substantially nonabsorbtivein this wavelength range. Suitable materials are synthetic or natural high polymers such as silicone, polystyrene, polyurethane, polyethylene, cellulose, polybutadiene, poly(methylmethacrylate), and polycarbonate. The preferred material is silicone.

Silicones are a large and well-known group of organosiloxane polymers based on a structure consisting of alternating silicon and oxygen atoms with various organic groups attached to the silicon:

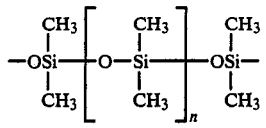

Silicones are preferred because of their extensive permeability to gases. For example, polydimethyl siloxane is reported to have a permeability to carbon dioxide at 30° C. of 3,240 CCS.(S.T.P.)/sqcm/cm/sec/cm Hg$\times 10^{10}$. Silicones are also preferred because they are adhesives and can be directly bonded to the distal end of an optical fiber. A preferred material is the silicone adhesive sold under the designation MDX 4210, lot #HH 125429, by Dow-Corning Corp., Midland, Mich. As shown in FIG. 3, a 2 mm path length of this silicone adhesive has a percent transmission of greater than 60% throughout the carbon dioxide absorption wavelength range.

The body of silicone adhesive can be formed at the distal end of the optical fiber by moulding Preferably, the silicone body is 1 mm in length and is coated at the distal end with a reflective coating, to produce a 2 mm absorption path length It has been found that a 2 mm path length will absorb about 50–60% of the incident signal at 40 mm Hg $CO_2$ When making concentration measurements, it is preferable to generate an output signal in the middle of the percent absorption range because such measurements are more accurate. Thus, a measurement in the range of about 25–75% absorption is preferred, and more preferably 30–70% absorption.

Although it is not required, a body permeable to carbon dioxide is likely to be permeable to all gases present in a fluid sample such as blood. However, as long as the other gases do not absorb radiation in the $CO_2$ absorption wavelength region, they will not affect the intensity of the relevant wavelength portion of the return signal.

The optical fiber must be substantially impermeable to carbon dioxide so that $CO_2$ absorption occurs only along the fixed path length of the body and not along some indeterminate length of the fiber in which $CO_2$ has diffused from the body into the fiber Furthermore, the fiber is substantially transparent at the predetermined wavelength range so that the reduction in intensity is due to $CO_2$ absorption and not to other losses within the system Suitable fibers include fluoride glass, chalcogenide glass, chloride glass, silver halide, and potassium halide. Preferred fibers are those fluoride glasses consisting of heavy metal fluoride (HMF) glasses which have optical and mechanical properties which surpass silica in some respects. These glasses have remarkably high transmission in the infrared region. For a description of such HMF glasses see P. C. Tran et al., "Heavy Metal Flouride Glasses And Fibers: A Review", Journal of Lightwave Technology, Vol. LT-2 No. 5, October, 1984. A preferred HMF fiber is available from Le Verre Fluore, Z. I. Du Champ Martin, Vern-Sur-Seiche, 35770 St., Erblon, France. The fiber consists of a 150 micrometer diameter core and 200 micrometer diameter cladding both made of zirconium fluoride glasses A UV cured acrylate coating is provided around the cladding. The fiber losses are reported to be below 1 dB/m between 1 and 4 micrometers. As shown in FIG. 3, a one meter length of this fiber has a percent transmission in the first wavelength range of greater than 70% in 40 mm Hg of $CO_2$.

The infrared source must be capable of producing radiation at least a portion of which is within the predetermined wavelength region. Furthermore, the source must be capable of coupling sufficient energy into the fiber so that in spite of the energy lost to the carbon dioxide and the energy lost in transmission, the return signal is of sufficient intensity to enable the detector to discriminate the same.

A suitable infrared detector would be lead selenide which has a peak detectivity near 4 micrometers, can be used at room temperature, and is quite inexpensive. The detector material has a typical NEP (noise equivalent power) of $10^{-10}$ watts, so that a received optical power level of about $10^{-7}$ watts would give a reasonable signal-to-noise ratio.

For use with such a detector, the infrared source must be capable of coupling at least about $10^{-5}$ watts into the fiber, since about 10 dB will be lost to the $CO_2$ and at least 10 dB will be lost in the return to the detector. This level of illumination is possible with an incoherent source, and is readily obtained with a minimal 100 microwatt laser.

A suitable incoherent source would be a 3,000° K. black body radiator having a spectral radiance of $10^5$ watts/(m$^2$ ster micrometer) at 4 micrometers. A typical 100 micrometer diameter fiber in contact with this radiator will accept about 0.3 steradian over its $10^{-8}$ m$^2$ face. The usable spectral segment is roughly the half-width of the carbon dioxide band (0.1 micrometers). Discarding all of the radiation outside this band by a simple filter or dispersive device will produce about $10^{-5}$ watts in the fiber if the filter losses do not exceed 5 dB.

Alternatively, a laser can be used as the source of infrared radiation. Use of a laser source will eliminate the need for the narrowband filter 36, but a focusing lens 38 is still required to get the energy into the fiber. A laser source is preferred, where the expense is warranted, because it produces a higher power, less noisy signal at the detector.

Semiconductor lasers, such as lead salts, or lead chalcogenide, can be fabricated to operate throughout the infrared spectrum. A composition of $PbS_{1-x}Se_x$ operating with a 500 microwatt output near 4.25 micrometers is commercially available. These lasers have very narrow line widths of about $10^{-3}$cm$^{-1}$. However, the output wavelengths are highly temperature sensitive, necessitating a well-controlled cryogenic environment. Thus, this source would be useful only under controlled temperature conditions.

Other semiconductor lasers include Group III-V alloys such as the double heterostructural AlGaAsSb having a band gap equivalent to 4.3 micrometers which can be lattice matched on GaSb substrates. Again, such devices would likely need to operate below room temperature.

Another suitable laser source is the cascade type $CO_2$ laser, a simple variation of the conventional 10 micrometer $CO_2$ laser. The smallest and simplest of these is capable of delivering about 100 milliwatts on one or several of these closely spaced lines. Of necessity, the available laser frequencies are slightly offset from and fall in between the frequencies which make up the $CO_2$ absorption band. In effect, the laser output would pass cleanly through a substantial length of low pressure CO2 gas, even though their spectral envelopes are largely overlapped. However, a sample of blood gases and water vapor at a total pressure of 0.3 atmospheres may induce sufficient broadening of the absorption lines to bring the absorption up to appreciable levels. Thus, a 4.3 micrometer $CO_2$ laser would provide a suitable energy source where carbon dioxide was to be measured in the presence of other blood gases and water vapor, such as during in vivo use.

By measuring the change in intensity caused by passing an energy signal through a fixed length body containing an unknown concentration of a certain component, the concentration of that component can be determined where the length of the body and absorption coefficient for the component are known. The relationship, known as Beer's Law, provides:

$$\frac{I}{I_0} = e^{-\epsilon cl}$$

where $I_0$ is the intensity of the incident energy signal, I is the intensity of the emitted or return signal, $\epsilon$ is the absorption coefficient for the component, l is the path length of the energy signal through the body, and c is the concentration of the component in molecules per volume. The logarithm of the inverse of the ratio $I/I_o$ is also known as the absorbance.

In the sensor illustrated embodiment of this invention, the path length is twice the length of the body. The ratio of $I/I_o$ is determined by the detector. At its maximum, the absorption coefficient of the envelope for the predetermined wavelength range of carbon dioxide is about 100 $cm^{-1} atm^{-1}$. This value will produce a unity optical absorbance in a 2 millimeter pathlength of carbon dioxide at the relevant partial pressure of 0.05 atm. The path length can be set to produce an intensity ratio of about 0.3 at a physiological concentration of $CO_2$ If the path length is too short or the concentration low, the ratio of intensities will be approximately one because insufficient absorption has taken place for a proper reading. Alternatively, if the path length is too long or the concentration too large, the intensity ratio will drop to zero because there has been a total absorption. Thus, the path length must be set somewhere between these outer limits based upon the concentration level and path length in order to generate an observable change in intensity ratio. It is preferred that this range lie between 0.20 and 0.80, and more preferably between 0.30 and 0.70.

According to another aspect of this invention, a method is provided for determining the concentration of the gaseous component in a fluid, such as a liquid or a gaseous medium. According to the method, a solid body of a natural or synthetic high polymer is exposed to the fluid containing the gaseous component, the body is exposed to infrared radiation, and the infrared absorption by the gas in the body is measured. The polymer must have a high affinity for the gaseous component of interest and must be substantially transparent to the wavelength of infrared radiation absorbed by the gaseous component. The polymer should have a solubility of at least 0.01 cc of gas per cc of polymer per atm. Suitable polymers include silicone rubber, polystyrene, polyurethane, polyethylene, cellulose, polybutadiene, poly(methylmethacrylate), and polycarbonate. The method is useful for determining the concentration of gases which have an absorption band in the infrared range, such as carbon dioxide, water vapor, nitrous oxide, halogenated hydrocarbons, ethyl alcohol, and various anesthetic gases. In a preferred embodiment, silicone rubber, which has a $CO_2$ solubility of 2.0 cc of gas per cc of polymer per atm, is used for measuring the concentration of carbon dioxide in the blood.

While certain preferred embodiments of the invention have hereinbefore been described, it will be appreciated that variations of the invention will be perceived by those skilled in the art, which variations are nevertheless within the scope of the invention as defined by the claims appended hereto.

What is claimed is:

1. Analytical apparatus comprising:
   waveguide means defining an axially-elongated energy path having an inlet aperture receptive to an incident energy signal within a predetermined wavelength range and an emission aperture for emitting an emitted energy signal, said waveguide means allowing passage of and being substantially transparent to energy within eh predetermined wavelength range;
   an axial segment of said waveguide means comprising a block of fixed axial length of a solid material which is substantially transparent to energy within the predetermined wavelength range and permeable to a gaseous component that has an energy absorption peak in the predetermined wavelength range, the remainder of said waveguide means being substantially impermeable to the gaseous component;
   whererin, when said axial segment is exposed along said fixed length to a fluid containing the gaseous component; the gaseous component permeates said segment and absorbs the incident energy signal along said fixed length to thereby reduce the intensity of the emitted energy signal in proportion to the concentration of the gaseous component in the segment, whereby differnces between the intensities of the incident and emitted energy signals may provide an indication of the concentration of the gaseous component in the fluid.

2. The apparatus of claim 1, wherein
   said waveguide means comprises an optical fiber having a distal end with said block disposed along its axial length.

3. The apparatus of claim 2, wherein
   said block has first and second ends, wherein said first end is disposed at the distal end of said optical fiber and said second end contacts a reflective surface.

4. The apparatus of claim 1, wherein
   said block comprises a solid polymeric material.

5. The apparatus of claim 4 for measuring the concentration of carbon dioxide in a fluid, wherein
   said optical fiber is made of a fluoride glass and said block is made of silicone and said fiber and block are substantially transparent to a predetermined wavelength range of from about 4.1 to about 4.4 micrometers.

6. Analytical apparatus comprising:
   a catheter body having a distal end positionable in vivo,
   waveguide means carried by the catheter body and defining an axially-elongated energy path having an inlet aperture for receiving an incident energy signal within a predetermined wavelength range and an emission aperture for emitting an emitted energy signal, said waveguide means allowing passage of and being substantially transparent to energy within the predetermined wavelength range;

an axial segment of said waveguide means comprising a block of fixed axial length of a solid material which is substantially transparent to energy within the predetermined wavelength range and permeable to a gaseous component that has an energy absorption peak in the predetermined wavelength range, the remainder of said waveguide means being substantially impermeable to the gaseous component;

wherein, when said axial segment is exposed along said fixed length to a body fluid containing the gaseous component, the gaseous component permeates said segment and absorbs the incident energy signal along said fixed length to thereby reduce the intensity of the emitted energy signal in proportion to the concentration of the gaseous component in the segment, whereby differences between the intensities of the incident and emitted energy signals may provide an indication of the concentration of the gaseous component in the patient's body fluid.

7. The analytical apparatus of claim 6, wherein the waveguide means comprises an optical fiber having a distal end with said block disposed along its axial length.

8. the analytical apparatus of claim 7, wherein said block has first and second ends, wherein said first end is disposed at the distal end of the fiber and said second end contains a reflective surface.

9. The analytical apparatus of claim 8 for measuring the concentration of carbon dioxide in the blood, wherein said optical fiber is made of a fluoride glass and said block is made of silicone and said fiber and block are substantially transparent to a predetermined wavelength range of from about 4.1 to about 4.4 micrometers.

10. The analytical apparatus of claim 6, wherein said catherter has an aperture adjacent its distal end and said block is disposed adjacent said aperture so as to allow contact with body fluid.

11. A system for measuring the concentration of a gaseous component in a fluid by absorption, the gaseous component having an energy absorption peak lying within a predetermined wavelength range, said system comprising:

waveguide means defining an axially-elongated energy path having an inlet aperture receptive to an incident energy signal within the predetermined wavelength range and an emission aperture for emitting an emitted energy signal, said waveguide means for allowing passage of and being substantially transparent to energy within the predetermined wavelength range;

an axial segment of said waveguide means comprising a block of fixed axial length of a solid material which is substantially transparent to energy within the predetermined wavelength range and permeable to a gaseous component to be measured, the remainder of said waveguide means being substantially impermeable to the gaseous component;

wherein, when said axial segment is exposed along said fixed length to a fluid the gaseous component to be measured will permeate said segment and absorb an incident energy signal along said fixed length to thereby reduce the intensity of an emitted energy signal in proportion to the concentration of the gaseous component in the segment;

energy source means for directing to said inlet aperture the incident energy signal;

a detection means and means for directing the emitted energy signal from said emission aperture to said detection means, said detection means being constructed and arranged to provide an indication of the concentration of the gaseous component in the fluid as a function of the intensity of the emitted every signal.

12. A fiber optic sensor for measuring the concentration of a gaseous component in a fluid by absorption, the gaseous component having an energy absorption peak lying within a predetermined wavelength range, said sensor comprising:

an optical fiber which is substantially impermeable to the gaseous component and substantially transparent to the predetermined wavelength range, said fiber being axially-elongated and having a proximal end and a distal end, the proximal end being coupled to means for inputting an incident energy signal within the predetermined wavelength range and being further arranged to emit an emitted energy signal;

a block of fixed axial length disposed at the distal end of said fiber, said block being made of a solid material which is substantially transparent to the predetermined wavelength range and permeable to the gaseous component, said block having a first end coupled to said distal end of said fiber and a second end having an inwardly reflective surface, wherein, when said block is exposed to the fluid along said fixed length the gaseous component permeates said block and absorbs the incident energy signal as it travels along said fixed length to thereby reduce the intensity of the emitted energy signal in proportion to the concentration of the gaseous component in the block, and means for detecting the emitted signal for measuring differences between the intensities of the incident and emitted signals and for providing an indication of the concentration of the gaseous component in the fluid based on said differences.

13. The fiber optic sensor of claim 12 for measuring the concentration of carbon dioxide in a fluid wherein said optical fiber and block are substantially transparent to a predetermined wavelength range which corresponds to an absorption peak for carbon dioxide.

14. The fiber optic sensor of claim 13, wherein said fiber and block are substantially transparent to a predetermined wavelength range of from about 4.1 to about 4.4 micrometers.

15. The fiber optic sensor of claim 14, wherein said fiber is made of a material selected from the group consisting of fluoride glass, chalcogenide glass, chloride glass, silver halide, and potassium halide; and said block is made of a material selected from the group consisting of silicone, polystyrene, polyurethane, polyethylene, cellulose, polybutadiene, poly(methylmethacrylate), and polycarbonate.

16. The fiber optic sensor of claim 15, wherein said fiber is a heavy metal fluoride glass and said block is silicone.

17. The fiber optic sensor of claim 16 for measuring a partial pressure of carbon dioxide of from about 10 to about 100 mm Hg, wherein
said block has a length of from about 0.5 to about 2 mm.

18. The fiber optic sensor of claim 17, wherein
said block has a length of about 1 mm.

19. The fiber optic sensor of claim 12, wherein
said second end of said block is covered with a reflective metal coating.

20. The fiber optic sensor of claim 12, wherein
substantially the entire outer surface of said block, other than said first end, is at least partially covered by a reflective metal coating.

21. The fiber optic sensor of claim 12, wherein
said block comprises a cylinder coaxially adhered to the distal end of the fiber.

22. The fiber optic sensor of claim 12, wherein
said block comprises a cylinder of silicone coaxially adhered to the distal end of the fiber.

23. The fiber optic sensor of claim 12, wherein
said fiber and block are disposed within a flexible catheter adapted for insertion in a body cavity for making an in vivo determination of the concentration of a gaseous component in a body fluid.

24. The fiber optic sensor of claim 12, wherein
said fiber and block are disposed within a flexible catheter adapted for insertion in the bloodstream of a patient for making an in vivo determination of the concentration of a gaseous component in the blood.

25. A method for detecting a gaseous component in a fluid by absorption, the gaseous component having an energy absorption peak lying within a predetermined wavelength range, said method comprising the steps of:
directing an incident energy signal within said predetermined wavelength range to an inlet aperture of an axial waveguide means, the waveguide means allowing passage of and being substantially transparent to energy in the predetermined wavelength range and being substantially impermeable to the gaseous component except for a fixed-length axial segment thereof comprising a block of solid material which is permeable to the gaseous component;
exposing said axial segment along the fixed length thereof to a fluid containing the gaseous component, wherein the gaseous component permeates the segment;
passing the incident energy signal through said waveguide means, wherein the incident energy signal is absorbed by the gaseous component along the fixed length of the axial segment to thereby reduce the intensity of the emitted energy signal in proportion to the concentration of the gaseous component in the segment;
detecting the emitted energy signal from an emission aperture of said waveguide means; and determining the concentration of the gaseous component from the detected emitted energy signal.

26. The method of claim 25 for measuring the concentration of a gase having an energy absorption peak in the infrared region, wherein
an incident energy signal having a wavelength in the infrared region is directed to the inlet aperture.

27. The method of claim 26 wherein said gaseous component is selected from the group consisting of carbon dioxide, water vapor, nitrous oxide, halogenated hydrocarbon, ethyl alcohol, and anesthetic gases, and wherein
the incident energy signal is selected to have a wavelength corresponding to an absorption peak of the selected gas.

28. The method of claim 27, for the measurement of the carbon dioxide concentration in blood, wherein
an incident energy signal having a wavelength of from about 4.1 to about 4.4 micrometers is directed to the inlet aperture.

* * * * *

UNITED STATES PATENT AND TRADEMARK OFFICE
CERTIFICATE OF CORRECTION

PATENT NO. : 4,800,886

DATED : January 31, 1989

INVENTOR(S) : James R. Nestor

Page 1 of 2

It is certified that error appears in the above-identified patent and that said Letters Patent is hereby corrected as shown below:

Col. 8, line 39 - After "laser" insert -- . --

Col. 8, line 41 - After "band" insert -- . --

Col. 8, line 62 - Delete "nonabsorptivein" and substitute -- nonabsorptive in --

Col. 9, line 24 - After "moulding" insert -- . --

Col. 9, line 29 - After "$CO_2$" insert -- . --

Col. 9, line 46 - After "fiber" insert -- . --

Col. 9, line 50 - After "system" insert -- . --

Col. 9, line 65 - After "glasses" insert -- . --

Col. 11, line 37 - After "$CO_2$" insert -- . --

Col. 12, line 21 - Delete "eh" and substitute -- the --

Col. 12, line 32 - Delete "whererin" and substitute -- wherein --

Col. 12, line 34 - Delete ";" and substitute -- , --

Col. 12, line 39 - Delete "differnces" and substitute -- differences --

Col. 12, line 49 - Delete "contacts" and substitute -- contains --

UNITED STATES PATENT AND TRADEMARK OFFICE
CERTIFICATE OF CORRECTION

PATENT NO. : 4,800,886

DATED : January 31, 1989

INVENTOR(S) : James R. Nestor

It is certified that error appears in the above-identified patent and that said Letters Patent is hereby corrected as shown below:

Column 16, line 22, "gase" should read -- gas --.

Signed and Sealed this

Eighteenth Day of July, 1989

Attest:

DONALD J. QUIGG

Attesting Officer

Commissioner of Patents and Trademarks